(12) United States Patent
Rouvinen et al.

(10) Patent No.: US 11,679,152 B2
(45) Date of Patent: Jun. 20, 2023

(54) RECOMBINANT HYPOALLERGENIC EQU C 1 POLYPEPTIDES FOR USE IN THE IMMUNOTHERAPY OF HORSE ALLERGY

(71) Applicant: Desentum Oy, Espoo (FI)

(72) Inventors: Juha Rouvinen, Espoo (FI); Kristiina Takkinen, Espoo (FI); Marja-Leena Laukkanen, Espoo (FI); Merja Niemi, Espoo (FI); Janne Jänis, Espoo (FI); Jaana Haka, Espoo (FI)

(73) Assignee: Desentum Oy, Espoo (FI)

( * ) Notice: Subject to any disclaimer, the term of this patent is extended or adjusted under 35 U.S.C. 154(b) by 128 days.

(21) Appl. No.: 16/959,156

(22) PCT Filed: Jan. 4, 2019

(86) PCT No.: PCT/FI2019/050002
§ 371 (c)(1),
(2) Date: Jun. 30, 2020

(87) PCT Pub. No.: WO2019/135027
PCT Pub. Date: Jul. 11, 2019

(65) Prior Publication Data
US 2020/0345839 A1    Nov. 5, 2020

(30) Foreign Application Priority Data
Jan. 4, 2018 (FI) .................................. 20185009

(51) Int. Cl.
*A61K 39/35* (2006.01)
*A61P 37/08* (2006.01)
*C07K 14/47* (2006.01)

(52) U.S. Cl.
CPC .............. *A61K 39/35* (2013.01); *A61P 37/08* (2018.01); *C07K 14/47* (2013.01)

(58) Field of Classification Search
None
See application file for complete search history.

(56) References Cited

U.S. PATENT DOCUMENTS

2009/0297564 A1    12/2009    Hernandez et al.

FOREIGN PATENT DOCUMENTS

| CN | 102617726 A | 8/2012 |
|---|---|---|
| EP | 1812059 B1 | 5/2010 |
| EP | 2114996 B1 | 5/2015 |
| WO | WO2004047794 A2 | 6/2004 |
| WO | WO2008092992 A1 | 8/2008 |
| WO | WO2008098277 A2 | 8/2008 |
| WO | WO2009153414 A1 | 12/2009 |
| WO | WO2012143374 A1 | 10/2012 |

OTHER PUBLICATIONS

Blumenthal et al.*
Sailer et al. 'Molecular ensembles make evolution unpredictable.' PNAS 114(45):11938-11943, 2017.*
Kuby Immunology, 4th Edition, Chapter 18, "Vaccines." pp. 449-465, 2001.*
Allen: Remington: The Science and Practice of Pharmacy: From the Past into the Future. Remington's Pharmaceutical Sciences, Sep./Oct. 2012, vol. 16, No. 5.
Arango et al: Eur J Biochem, 1992, vol. 205, No. 2, pp. 575-581.
Database Genbank: Equus asinus major allergen Equ c 1-like (LOC106842740), mRNA. Dec. 2, 2015. Accession No. XM_014859441.1.NCBI.
Database Genbank: Equus caballus major allergen Equ c 1-like (LOC100056556), mRNA. Sep. 22, 2013. Accession No. XM_001490249.2.NCBI.
Database Genbank: Equus przewalskii major allergen Equ c 1-like (LOC103546844), mRNA. Jul. 14, 2014. Accession No. XM_008513730.1 NCBI.
Database UniProt: Jul. 27, 2011. 11 SubName: Full= Uncharacterized protein {EC0:00a0313IEnsembl:ENSECAP00000008188}. XP002789310, retrieved from EBI accession No. Uni Prot: F6PJ64 Database accession No. F6PJ64.
Goubran Botros et al: Biochemical characterization and surfactant properties of horse allergens. Eur. J. Biochem, 2001, vol. 268, pp. 3126-3136.
Gregoire et al: cDNA Cloning and Sequencing Reveal the Major Horse Allergen Equ cI to Be a Glycoprotein Member af the Lipocalin Superfamily. Journal of Biological Chemistry, Dec. 20, 1996, vol. 271, No. 51, pp. 32951-32959.
Hoffmann-Sommergruber et al: High-level expression and purification of the major birch pollen allergen, Bet v 1. Protein Expr Purif, 1997, vol. 9, No. 1, pp. 33-39.
Immonen et al: The major horse allergen Equ c 1 contains one immunodominant region af T cell epitopes. Clinical & Experimental Allergy : Journal of the British Society for Allergy and Clinical Immunology, Jun. 1, 2007, vol. 37, No. 6, pp. 939-947.
Lascombe et al: Crystal structure of the allergen Equ c 1. A dimeric lipocalin with restricted IgE-reactive epitopes. The Journal of Biological Chemistry, Jul. 2000, vol. 275, No. 28, pp. 21572-21577.
Laver et al: Epitopes on Protein Antigens: Misconceptions and Realities. Cell, 1990, vol. 61, pp. 553-556.
Niederberger et al: Vaccination with genetically engineered allergens prevents progression of allergic disease. PNAS, 2004, vol. 101, No. 2, pp. 14677-14682.
Niemi et al: Molecular Interactions between a Recombinant IgE Antibody and the b-Lactoglobulin Allergen. Structure, 2007, vol. 15, pp. 1413-1421.

(Continued)

*Primary Examiner* — Nora M Rooney
(74) *Attorney, Agent, or Firm* — Laine IP Oy

(57) ABSTRACT

The present invention relates to specific modified Equ c 1 polypeptides and to the use of such polypeptides as hypoallergens for desensitizing against horse allergy. Particularly, the present invention provides a recombinant hypoallergenic Equ c 1 polypeptide comprising at least two amino acid modifications compared to a corresponding wild type Equ c 1 allergen, wherein the recombinant hypoallergenic polypeptide activates release of histamine from basophils to a degree less than the wild type allergen.

11 Claims, 9 Drawing Sheets

Specification includes a Sequence Listing.

(56) References Cited

OTHER PUBLICATIONS

Rouvinen et al: Transient Dimers of Allergens. PloS One, Feb. 2010, vol. 5, Issue 2, e9037.
Stancombe et al: Isolation of the gene and large-scale expression and purification of recombinant Erythrina cristagalli lectin. Protein Expr Purif, 2003, vol. 30, No. 2, pp. 283-292.
Trevino et al: Amino acid contribution to protein solubility: Asp, Glu, and Ser contribute more favorably than the other hydrophilic amino acids in RNase Sa. Journal of Molecular Biology, 2007, vol. 366, pp. 449-460.
Tuschl: Expanding small RNA interference. Nat. Biotechnol, May 2002, vol. 20, pp. 446-448.

* cited by examiner

RECOMBINANT HYPOALLERGENIC EQU C 1 POLYPEPTIDES FOR USE IN THE IMMUNOTHERAPY OF HORSE ALLERGY

FIELD OF THE INVENTION

The present invention is related to the field of allergic (hypersensitivity) diseases and to protein engineering technology for producing modified allergenic polypeptides (hypoallergens) for use in the immunotherapy of horse allergy. Particularly, the present invention relates to specific modified Equ c 1 polypeptides and to the use of such polypeptides as hypoallergens for desensitizing against horse allergy. Furthermore, the invention relates to pharmaceutical and vaccine formulations comprising said polypeptides.

BACKGROUND OF THE INVENTION

Allergic diseases, for example, asthma, rhinitis, eczema and food allergies are reaching epidemic proportions in the world. These type I hypersensitive reactions are based on the formation of immunoglobulin E (IgE) antibodies against, in principle, harmless antigens, allergens. The symptoms occur when an allergen molecule binds to two IgE antibodies bound to receptors on a mast cell or basophile surface and induces crosslinking of the IgE-FcεRI complexes. This triggers the degranulation of biological mediators, such as histamine and lipid mediators, which cause inflammatory reactions and symptoms.

Horse allergy occurs in people who regularly work with horses, either professionally or for recreational purposes, and also in people indirectly exposed to horses. Horse allergy is induced by exposure to the horse allergens, such as Equ c 1, c2, c3, c4 and c 5. Of these Equ c 1, a major horse allergen, is a hair dander protein and the most important from a clinical perspective. Structurally, Equ c 1 (molecular weight 25 kD) is a glycoprotein member of the lipocalin protein family and is synthesized in the liver and in the sublingual and submaxillary salivary glands. Equ c 1 is responsible for about 80% of anti-horse IgE antibody response in patients who have been exposed to horse allergens (Goubran Botros et al., 2001, Eur. J. Biochem, 268: 3126-3136).

The essential questions when studying allergenicity involves the so called B-cell epitope, the IgE antibody-binding site of an allergen, and currently also dimeric structures found in many allergens.

Niemi et al., Structure 2007(15): 1413-21, disclose one approach in the search of specific allergen epitopes in the line with the disclosure of layer et al., Cell 1990(61):553-556, who state that the only rational method by which to determine the complete epitope of any allergen involves measuring crystal structure of an allergen in complex with an IgE antibody. Niemi et al. disclose the crystal structure of an IgE Fab fragment in complex with β-lactoglobulin (BLG). They also show how two IgE/Fab molecules bind the dimeric BLG and that the IgE epitope is different when compared to known IgG epitope structures, being a "flat" surface located in the β sheet regions.

Relating to the modification of the IgE epitope in an allergen, international patent publication WO 2008/092992 discloses a method of blocking the type I surface interaction of allergenic substances by modifying amino acid residues on non-continuous allergenic epitopes, i.e., on a planar surface with an area of 600-900 $Å^2$ on the allergenic substance.

Rouvinen et al., PloS ONE 2010(5):e9037 investigated the role of dimeric structures of allergens using bioinformatics methods combined with native mass spectrometry. (Electrospray Ionization Fourier Transform Ion Cyclotron Mass Spectrometry, ESI FT-ICR-MS). The 55 known crystal structures of allergens were studied by PISA server from the European Bioinformatics Institute showing that 80% of them exist in symmetric dimers or oligomers in crystals and that the majority is transient dimers that are formed at high protein concentrations. ESI FT-ICR mass spectra analysis of nine different allergens confirmed dimerization of these allergens at higher concentrations in solution. The possible relationship between dimeric structure and allergenicity was studied with a recombinant allergen from cow's milk, β-lactoglobulin (rBos d 5 B), which occurs as a dimer, and its mutant H146P, which occurs mainly as a monomer. A somewhat reduced histamine releasing capacity was observed with the monomeric rBos d 5 B mutant H146P when compared to the native Bos d 5 B and recombinant Bos d 5 B. Although the authors conclude that dimerization could be a very common and essential feature for allergens and generally suggest that the preparation of purely monomeric variants of allergens could open up novel possibilities for specific immunotherapy, the ultimate role of structural features in allergenicity remain unknown. From the crystal analysis in which protein molecules are packed against each other in strictly ordered arrangement, direct conclusions as to how the allergen molecules behave in a human body, i.e. in vivo, cannot be drawn. Relating to the dimer formation in an allergen, international patent publication WO 2009/153414 discloses a method for preparing a hypoallergen for immunotherapy by altering the surface area of an allergen related to the formation of transient dimers or oligomers, i.e. the monomer-monomer interface, in order to inactivate or reduce the polypeptide's natural ability to form transient dimers or oligomers.

The trends in the treatment of all allergic symptoms have been towards an active induction of tolerance using allergen-specific desensitization instead of avoiding the allergen, which is often not possible, or merely treating the symptoms. Current desensitization therapy is based on allergens purified from natural sources, wherein batch to batch variations both in amounts of allergen components as well as other non-allergen protein substances may lead to problems related to finding and maintaining the right dosage and efficiency of the treatment. These problems lead to a potential risk of anaphylactic side effects and sensitization to new allergens.

The use of recombinant allergens for desensitizing would remove the disadvantages related to batch to batch variations and minimize the amount of other protein components which may cause side-effects or unwanted activation of immune system towards these impurity proteins. There is thus a recognized and large need for safe and efficient vaccines and therapy products to meet the increasing medical problem of allergy. At present the market for safe and efficient therapies of allergy is still underdeveloped.

SUMMARY OF THE INVENTION

In the present invention, recombinant hypoallergenic Equ c 1 polypeptides suitable for use in immunotherapy are provided for the first time. The hypoallergens of the present invention are designed so that both IgE-binding epitope and monomer-monomer interface are modified resulting in a hypoallergenic polypeptide that still has a native-like structure and thus immunogenic potential to develop protective IgG antibodies. However, the hypoallergen prevents the allergen induced crosslinking of the IgE-FcεRI complexes on a mast cell or basophile surface antibodies and hence decreases the release of histamine from basophils compared to the wild type allergen.

Accordingly, it is an aim of the present invention to provide a recombinant hypoallergenic Equ c 1 polypeptide comprising at least two amino acid modifications compared to a corresponding wild type Equ c 1 allergen, wherein the recombinant hypoallergenic polypeptide activates release of histamine from basophils to a degree less than the wild type allergen, wherein said amino acid modifications are amino acid substitutions at positions defined by the Equ c 1 wild type sequence of SEQ ID NO:1, wherein said polypeptide comprises at least one amino acid substitution at a position selected from the group consisting of: E21 and V47, and at least one amino acid substitution at a position selected from the group consisting of: V110 and F112.

The present invention also provides a pharmaceutical composition comprising the recombinant hypoallergenic Equ c 1 polypeptide according to the invention and at least one of the following: physiologically acceptable adjuvant, carrier, diluent, excipient, preservative and stabilizer.

Another aim of the present invention is to provide a method of treating horse allergy in a subject, the method comprising: administering to the subject an amount of the recombinant hypoallergenic Equ c 1 polypeptide according to the invention in an amount effective to ameliorate at least one symptom or clinical sign of allergy to the Equ c 1 allergen, wherein the recombinant hypoallergenic Equ c 1 polypeptide activates release of histamine from basophils to a degree less than the wild type allergen.

Another aim of the present invention is to provide a method of producing a recombinant hypoallergenic Equ c 1 polypeptide for immunotherapy comprising the steps of:

a) modifying the nucleic acid sequence encoding a wild type Equ c 1 polypeptide in order to substitute at least two amino acids at positions defined by the Equ c 1 wild type sequence of SEQ ID NO:1, wherein the nucleic acid sequence encoding a wild type Equ c 1 polypeptide is modified so that at least one amino acid substitution is formed at a position selected from the group consisting of: E21 and V47, and at least one amino acid substitution is formed at a position selected from the group consisting of: V110 and F112; and b) expressing or producing the recombinant Equ c 1 polypeptide from the modified nucleic acid;

c) isolating and purifying the recombinant Equ c 1 polypeptide from step b).

DETAILED DESCRIPTION OF THE INVENTION

Figure 1:
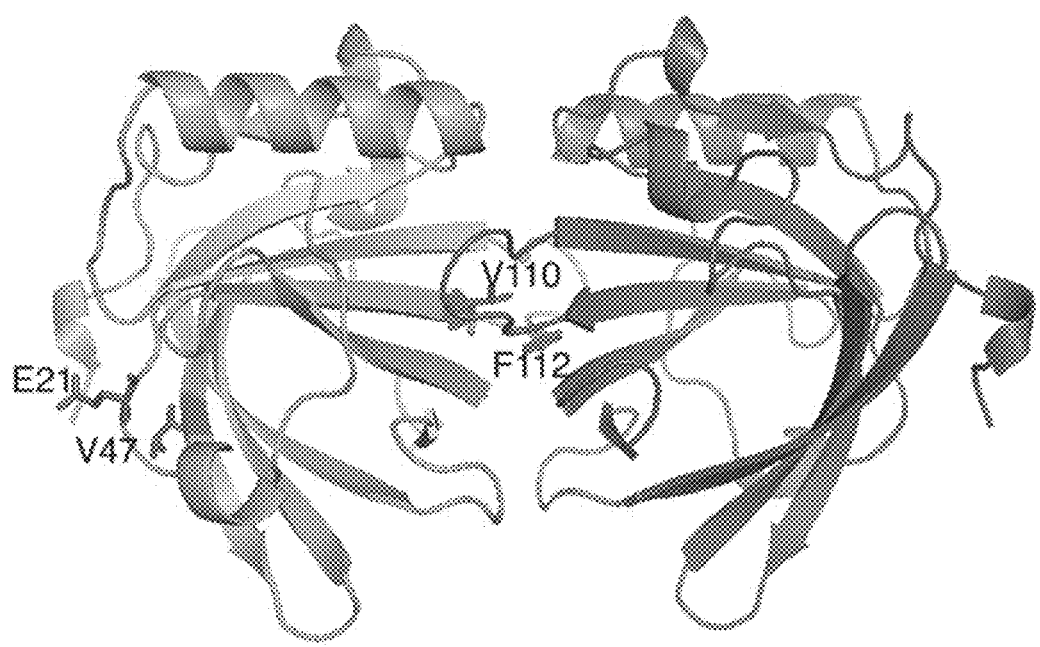
FIG. 1. The designed mutations of the Equ c 1 allergen. Mutations E21 and V47 are on the putative IgE epitope region and mutations V110 and F112 on the monomer-monomer interphase of dimeric Equ c 1 allergen.

In the present description, examples, claims and sequence listing both three-letter and one-letter codes may be used for amino acids. See, for instance, 1UPAC-IUB Joint Commission on Biochemical Nomenclature. Nomenclature and Symbolism for Amino Acids and Peptides. Eur. J. Biochem. 138:9-37(1984). The denomination of amino acid sites in the polypeptides according to the present disclosure are exemplified as follows: V47 means that there is a valine residue at position 47, whereas V47K means that the valine residue at position 47 has been replaced by a lysine residue.

The present invention provides mutated hypoallergenic polypeptide variants of Equ c 1, which are useful, e.g., as vaccines for immunizing subjects in need thereof and thus preventing and/or alleviating allergy and desensitizing subjects suffering from allergy against horse hair dander.

The recombinant Equ c 1 polypeptides according to the present invention have a wild type amino acid sequence, but additionally they contain amino acid substitutions at selected amino acid positions to reduce or fully diminish their ability to induce the production of IgE antibodies. However, it is important that mutated polypeptides still retain their capacity to induce the production of protective IgG antibodies which are active also against the corresponding folded wild type allergen.

Typical amino acid substitution providing the effect of the present invention would be the substitution of small residues with larger ones. In addition, the hydrophobic residues (like phenylalanine or leucine) could be replaced by hydrophilic residues (glutamic acid, lysine). In one preferred embodiment of the invention, there are altogether at least two, three or four amino acid substitutions. Preferably, the polypeptide of the invention has two, three, four, five, six, seven, eight, nine or ten substitutions. More preferably, the polypeptide has two, three or four substitutions. One of the advantages of the invention is that only a small number of substitutions are needed for the desired effects.

A person skilled in the art knows that nucleotide mutations leading to amino acid substitutions, additions and/or deletions at "non-essential" amino acid residues can also be made to the sequence of the wild type allergen, but this is not a particular aim of the present invention although the recombinant Equ c 1 polypeptides of the present invention may also comprise non-essential mutations, elongations, insertions and deletions in addition to the substitutions providing the effect of the present invention. A "non-essential" amino acid residue is a residue that can be modified in the wild-type sequences of Equ c 1 polypeptide without altering its biological activity or structure. Amino acids for which conservative substitutions can be made are well known in the art.

Further mutations conserving the biological activity but giving slightly modified physical properties, such as increased solubility, can also be introduced to the hypoallergenic polypeptide, see e.g. Trevino et al., 2007, Journal of Molecular Biology 366:449-460, disclosing amino acid modifications contributing to solubility of the modified protein.

The term "wild type Equ c 1" relates herein to the amino acid sequence as set forth in SEQ ID NO:1, isoforms thereof and to insertion/deletion variants thereof having the immunogenic potential of SEQ ID NO:1.

The hypoallergenic polypeptide variants of the present invention comprise variants, which contain substitutions affecting the IgE epitope of the Equ c 1 and also substitutions affecting dimer formation of the Equ c 1. For instance, positions E21 and V47 of SEQ ID NO:1 are related to the IgE epitope of Equ c 1 and positions V110 and F112 are related to dimer formation (see FIG. 1). Preferred substitutions for said positions are E21Y, V47K, V110E, V110D, F112R and F112K, but based on the present teaching a person skilled in the art is easily able to test the effect of other amino acid substitutions for said positions.

Accordingly, the present invention is directed to a recombinant hypoallergenic Equ c 1 polypeptide comprising at least two amino acid modifications compared to a corresponding wild type Equ c 1 allergen, wherein the recombinant hypoallergenic polypeptide activates release of histamine from basophils to a degree less than the wild type allergen, wherein said amino acid modifications are amino acid substitutions at positions defined by the Equ c 1 wild type sequence of SEQ ID NO:1, wherein said polypeptide comprises at least one amino acid substitution at a position selected from the group consisting of: E21 and V47, and at least one amino acid substitution at a position selected from the group consisting of: V110 and F112.

Preferably, said recombinant hypoallergenic Equ c 1 polypeptide comprises at least two or three amino acid substitutions and the preferred positions for said substitutions are a) E21, V110, and F112; b) V47, V110, and F112; c) E21 and V110; d) E21 and F112; e) V47 and V110; or f) V47 and F112.

The preferred amino acid substitutions for the above positions are E21Y, V47K, V110E, V110D, F112R and F112K.

Hypoallergenic variants according to the present invention are obtained by mutating chosen specific amino acid residues, e.g., residues with bulky side chains, located on the IgE binding epitope or monomer-monomer interface surfaces of Equ c 1. Preferably, the selected target amino acid residues are those, whose side chains point outside towards the solvent. Mutating such residues cause minimal change to the basic three-dimensional structure of the allergen. Preferably, however, the mutagenesis modifies the surface of the epitope or interface to such an extent that the binding and cross-linking of IgE antibodies on the mast cell surface is prevented or strongly reduced, while the overall structure of the variant is still very similar to that of the wild type allergen. Such a mutation favours the induction of IgG and other protective antibodies, having the ability of binding both to the wild-type allergen and to the mutated variant allergen. The effect of the mutation is determined as a lower affinity of the allergen specific IgE antibody towards the modified Equ c 1 allergen. Preferably the mutation decreases the affinity of the specific IgE antibody at least tenfold, preferably at least 20-fold, and more preferably 20- to 100-fold, and most preferably more than 100-fold. The resulting modified Equ c 1 allergen can be used to evoke tolerance against horse hair dander in allergic patients.

The hypoallergenic variant polypeptides according to the present invention, useful in allergen-specific desensitization, preferably possess the following two features: 1) the ability to strongly reduce an IgE-mediated reaction by hindering dimer formation and IgE binding to its epitope; and 2) a retained wild type 3D folding, and thus the capability of inducing the production of IgG-antibodies capable to bind wild type folded allergen.

As disclosed above, said recombinant hypoallergenic Equ c 1 polypeptide activates release of histamine from basophils to a degree less than the wild type allergen. Preferably, said histamine release capacity of the recombinant hypoallergenic polypeptide is at least 20 times reduced (i.e. up to 5% of the original activity is remaining), more preferably at least 100 times reduced (i.e. up to 1% of the original activity is remaining) when compared to the histamine release capacity of a wild type Equ c 1 allergen.

One important aim of the present invention is to provide a recombinant hypoallergenic Equ c 1 polypeptide for use in the treatment or prevention of horse allergy. The hypoallergenic polypeptides according to the present invention are thus useful as vaccines against horse allergy, especially horse hair dander allergy. Pharmaceutical compositions such as vaccines comprising polypeptides according to the present invention are formulated according to standard pharmaceutical procedures known to skilled persons in the art. Such compositions of the invention are prepared for storage by mixing the polypeptide having the desired degree of purity with optional physiologically acceptable carriers, excipients, preservatives or stabilizers (Remington's Pharmaceutical Sciences, 22nd edition, Allen, Loyd V., Jr, Ed., (2012)), e.g. in the form of lyophilized cake or aqueous solutions. For instance, a hypoallergen according to the present invention is formulated as conventional vaccine formulations, such as aluminum hydroxide adsorbed vaccines, using methods well known in the art (Niederberger et al., PNAS, 101 (2): 14677-82, 2004). Alternatively and preferably, however, the hypoallergens according to the present invention may be administered by other suitable vaccination routes and schemes, such as oromucosal or sublingual administration, using methods and formulations known in the art. See, e.g., European Patent publication EP 1812059.

The modified Equ c 1 hypoallergens could be used in concentrations of, e.g., 0.5 µg/ml, 5 µg/ml or 50 µg/ml. Exemplary doses may vary between 0.05 µg and 2 µg during a possible dosing-up phase, and between 3-15 µg during the maintenance phase, preferably 5-15 µg, most preferably about 10 µg, depending on the severity of the allergy, the age and medical history of the patient. A suitable dose is easily decided by a clinician familiar with treating and preventing allergy.

International patent publication WO04/047794 discloses a solid fast dispersing dosage form for sublingual administration of an allergy vaccine, and US patent application 2009/0297564 discloses a liquid vaccine formulation for oromucosal administration.

The modified Equ c 1 hypoallergens according to the present invention are particularly suitable for sublingual administration using sublingual drops. For this purpose the hypoallergenic polypeptides are provided in saline. A safe and effective dose range for administration of the polypeptides, as well as the dosing regimen capable of eliciting a desired immune response can be determined during clinical development of the vaccine candidates according to the present invention, using methods and schemes known in the art.

The present invention is also directed to a method of producing a recombinant hypoallergenic Equ c 1 polypeptide for immunotherapy, the method comprising the steps of:

a) modifying nucleic acid sequence encoding a wild type Equ c 1 polypeptide in order to substitute at least one amino acid at a position defined by the Equ c 1 wild type sequence of SEQ ID NO:1, wherein the position is selected from the group consisting of: E21, V47, V110 and F112; and b) expressing or producing the recombinant Equ c 1 polypeptide from the modified nucleic acid;

c) isolating and purifying the recombinant Equ c 1 polypeptide from step b).

Preferably, the above method comprises a further step of: d) testing the recombinant Equ c 1 polypeptide obtained from step b or c) for ability to activate release of histamine of an allergic reactions from human cells, wherein those the recombinant Equ c 1 polypeptides which do not activate histamine release or which activate histamine release less than the corresponding wild type Equ c 1 polypeptide are considered as hypoallergen candidates for immunotherapy.

Further, the above method may also comprise a step of: e) analysing that said recombinant Equ c 1 polypeptide has a native-like structure and immunogenic potential to develop protective IgG antibodies.

Preferably, the positions modified in step a) of the above method affect IgE epitope and/or dimer formation of the wild type Equ c 1. For instance, positions E21 and V47 of SEQ ID NO:1 are related to the IgE epitope of Equ c 1 and positions V110 and F112 are related to dimer formation (see FIG. 1). Both target areas are preferably modified. Preferred substitutions for said positions are E21Y, V47K, V110E, V110D, F112R and F112K, but based on the present teaching a person skilled in the art is easily able to test the effect of other amino acid substitutions for said positions.

Preferably, at least two or three amino acid substitutions are prepared in step a): at least one to a position selected from the group consisting of: E21 and V47, and at least one to a position selected from the group consisting of: V110 and F112. The preferred positions for said substitutions are a) E21, V110, and F112; b) V47, V110, and F112; c) E21 and V110; d) E21 and F112; e) V47 and V110; or f) V47 and F112.

The invention further provides a nucleic acid or polynucleotide encoding a recombinant hypoallergenic Equ c 1 polypeptide of the present disclosure and an expression vector comprising said nucleic acid and a host cell transformed with said vector. The selection of recombinant vectors suitable for expressing said nucleic acid or polynucleotide, methods for inserting nucleic acid sequences for expressing the polypeptide into the vector, and methods of delivering the recombinant vector to the host cells of interest are within the skill in the art. See, for example Tuschl, T. (2002), Nat. Biotechnol, 20: 446-448.

The following examples are given to further illustrate embodiments of the present invention, but are not intended to limit the scope of the invention. It will be obvious to a person skilled in the art, as technology advances, that the inventive concept can be implemented in various ways. The invention and its embodiments are thus not limited to the examples described herein, but may vary within the scope of the claims.

EXPERIMENTAL SECTION

Example 1. Design of Equ c 1 Mutations

The three-dimensional coordinates of Equ c 1 allergen (Protein Data Bank, accession code 1EW3) were downloaded to the appropriate molecular graphics program (such as Pymol, Chimera). The packing of protein molecules against each other were analyzed with the PISA server (www.ebi.ac.uk/pdbe/pisa) to detect putative monomer-monomer interfaces. Equ c 1 has one large monomer-monomer interface of 1025 Å$^2$ suggesting that Equ c 1 forms a very stable dimer. The largest interfaces were studied manually in three-dimensions by using a molecular graphics program. The central residues on the monomer-monomer interfaces were outlined. In the next step, theoretical mutations were made using the molecular graphics program to analyse which mutated side-chains would hinder packing of the second monomer thus hindering the formation of dimer. The IgE-epitope surface area was deduced to be located on the opposite site compared to the monomer-monomer interface area. Mutations on the putative IgE epitope surface were designed in such a way that the mutated residues (such as bulky or charged residue) would restrict the binding of an IgE antibody. By using this methodology, mutants V47K, E21Y were designed for the IgE epitope and V110E, V110D, F112K and F112R on the monomer-monomer interface (FIG. 1).

Example 2. Production of Recombinant Equ c 1 wt and Equ c 1 Mutants V47K-V110E-F112K, E21Y-V110E-F112K and E21Y-V110D-F112R in *Escherichia coli*

Synthetic gene fragments encoding Equ c 1 wt, Equ c 1 mutants V47K-V110E-F112K (Triple 2, SEQ ID NO:2), E21Y-V110E-F112K (Triple 3, SEQ ID NO:3) and E21Y-V110D-F112R (Triple 4, SEQ ID NO:4) with codon optimization for bacterial expression were purchased from Genescript. The amino acid sequences of Equ c1 wt and triple mutants 2, 3 and 4 are shown in the Sequence Listing as SEQ ID NOS:1-4. The synthetic gene fragments of Equ c 1 wt and its mutants were cloned as Nco I-Not I restriction fragments under the T7 promoter of the pET-28b(+) vector (Novagen) for cytoplasmic expression. The recombinant Equ c 1 allergens contain an extra alanine residue in the N-terminus due the usage of Nco I restriction site in the cloning of the synthetic genes. The Nco I cleavage site sequence (CCATGG) introduces the ATG codon of the methionine amino acid required for the translation initiation but also an additional G nucleotide. To be able to keep the open reading frame of the cloned Equ c 1 genes from the ATG codon a GCC codon coding an alanine amino acid was added into the 5' sequence of the Equ c 1 allergen genes. The pET-28b expression vectors were transformed into the *E. coli* BL21 (DE3) strain. Recombinant Equ c 1 wt and Triple 2, 3 and 4 were produced in 1.8 L shake flask cultivations. The unsoluble protein fraction was isolated from the cell pellet according to Hoffmann-Sommergruber et al. (1997) and refolding of the allergen polypeptides was performed according to Arango et al. (1992) and Stancombe et al. (2003).

Example 3. Purification of the Recombinant Equ c 1 Polypeptides

Recombinant Equ c 1 wt and the mutants were purified with a three-step chromatography procedure. The first step was an anion-exchange chromatography by a HiTrap DEAE Sepharose FF (GE Healthcare 17-5154-01) column, the second step a cationic-exchange chromatography by a HiTrap CM Sepharose FF (GE Healthcare 17-5056-01) column and the third step a size-exclusion chromatography (SEC) by a Tricorn™ Superdex™ 16/600 column (GE Healthcare). Fractions from the SEC column elution peak were analysed by a 18% Coomassie Brilliant-Blue stained SDS-PAGE showing that they were pure and homogeneous (data not shown). Elution peak fractions were pooled and concentration of the purified rEqu c 1 allergen determined by measuring $A_{280}$.

Figures 2A, 2B, 2C:
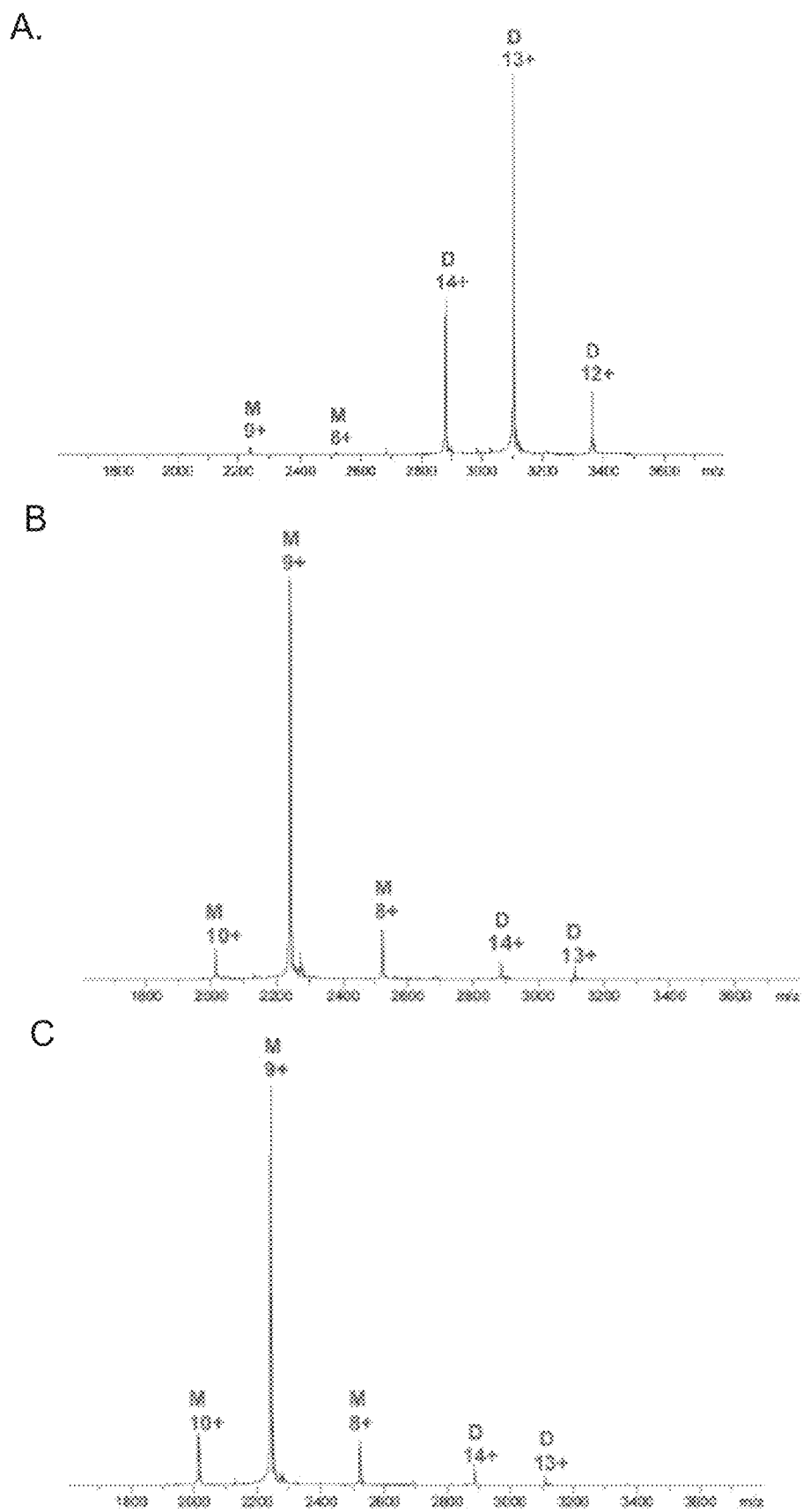
FIG. 2. The native ESI FT-ICR mass spectra of the recombinant wild-type Equ c 1 (A) and the recombinant Equ c 1 Triple 2 (B) and Triple 3 (C) mutants at a concentration of 40 μM. The peaks representing the protein monomer are marked with M and protein dimer with D.

Example 4. Analysis of Recombinant Equ c 1 and the Mutants by Mass Spectrometry The mass spectrometric experiments were performed with a 12T solariX XR mass spectrometer (Bruker Daltonics, Billerica, Mass., USA), equipped with an Apollo II ion funnel electrospray source. Before a mass spectrometric analysis, the protein sample was exchanged into an ESI-MS compatible ammonium acetate buffer (10 mM, pH 6.9) by using disposable PD-10 desalting columns (GE Healthcare). For mass spectrometric measurements in denaturing solution conditions, protein sample was diluted to 0.2 μM with acetonitrile/water/acetic acid solution. The protein solution was directly infused into the ion source by a syringe pump with a flow rate of 2 μl/min. The temperature of the drying gas was 200° C. and the pressure of the nebulizing gas was 1.0 bar. Mass spectra were acquired in the positive ion mode over the m/z range of 800-3000 with 1-Mword time-domain transients and 0.05 sec ion accumulation. In the native mass spectrometry, the instrumental parameters were carefully optimized to maintain non-covalent interactions in the gas-phase. Desalted protein samples were usually measured at a concentration of 40 μM in 10 mM ammonium acetate buffer. Typically, 100 co-added 256-kword time-domain transients were recorded and processed to 512-kword data prior to fast Fourier transform and frequency to mass conversion. The wild-type Equ c 1 allergen and the Equ c 1 mutants were measured using the same instrumental parameters, in order to avoid any bias between the protein samples. Mass calibration was done externally with respect to the ions of ES Tuning Mix (Agilent Technologies, Santa Clara, Calif., USA). The mass spectrometric data were acquired by using ftmsControl software and processed with the use of Data Analysis 4.4 software (Bruker Daltonics). The high resolution denatured and native mass spectra of wt rEqu c 1 and Triple 2 and 3 mutants are shown in FIG. 2. The native mass spectra results clearly show that rEqu c 1 Triple 2 and 3 mutants exist mainly as monomers whereas wt rEqu c 1 exists mainly as a dimer at the concentration of 40 μM.

Figures 3A, 3B, 3C:
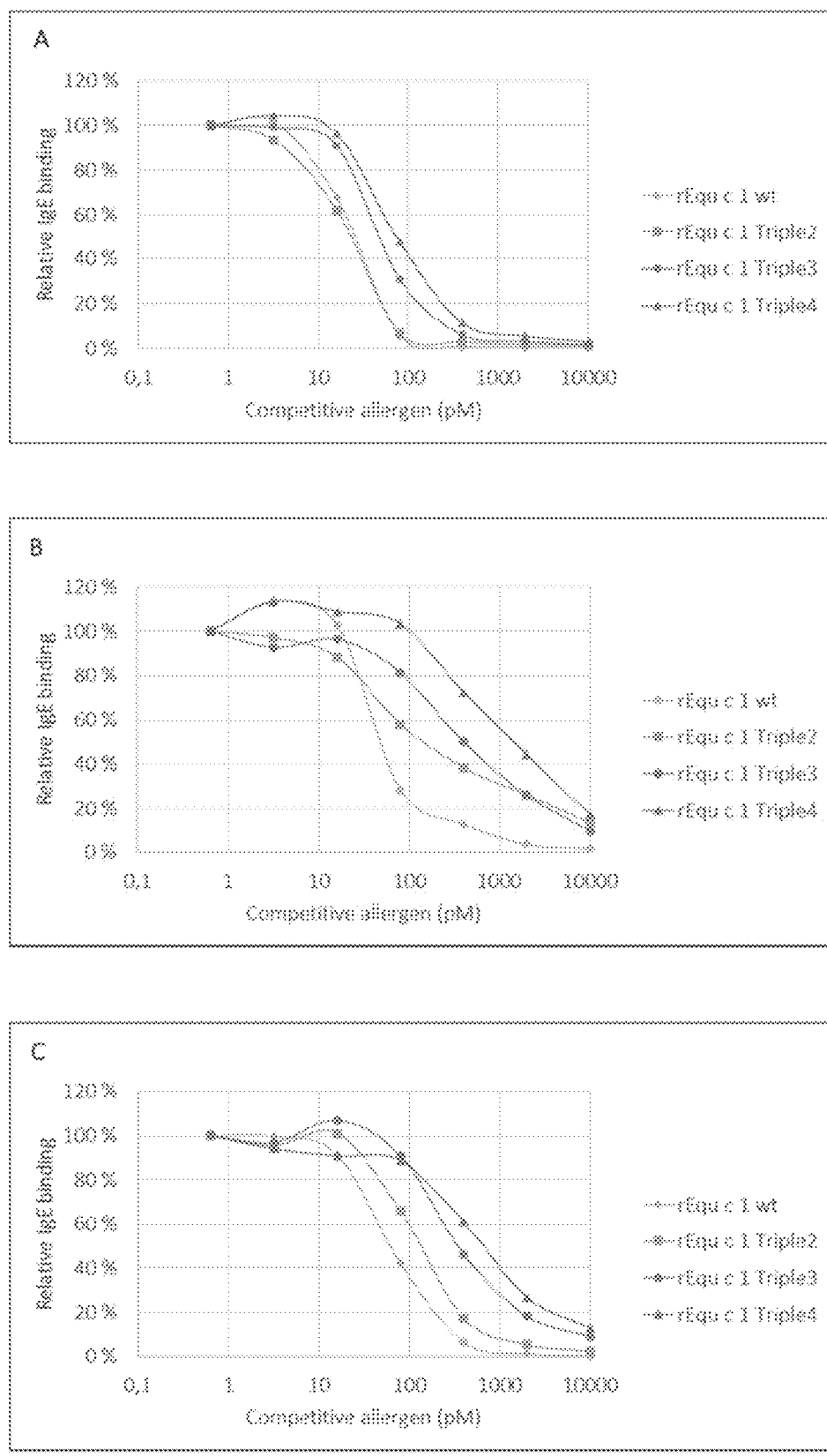
FIG. 3 shows the result of the competitive immunoassay measuring the inhibition of serum IgE binding to rEqu c 1 wt obtained from five allergic patients (panels A-E) with increasing soluble concentrations of rEqu c 1 wt, Triple 2, Triple 3 and Triple 4 mutants.
Figure 3D:
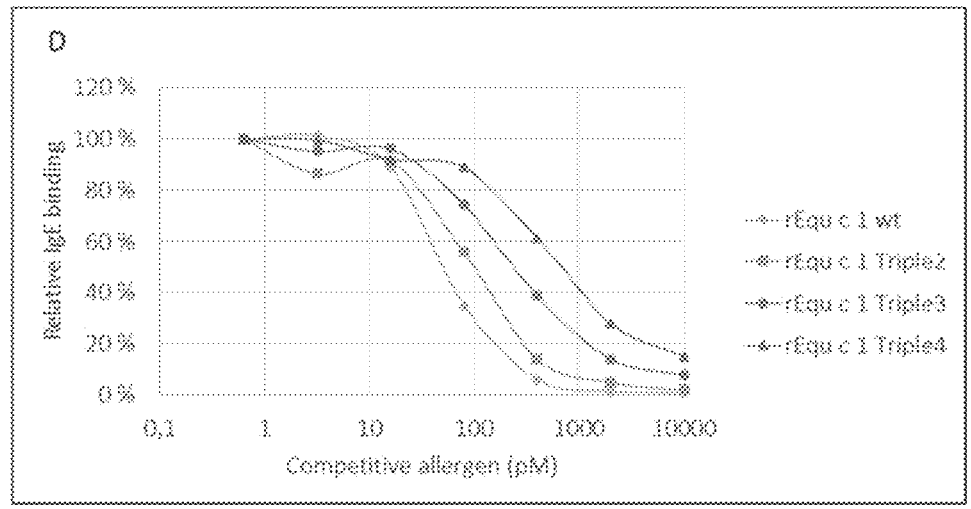
Figure 3E:
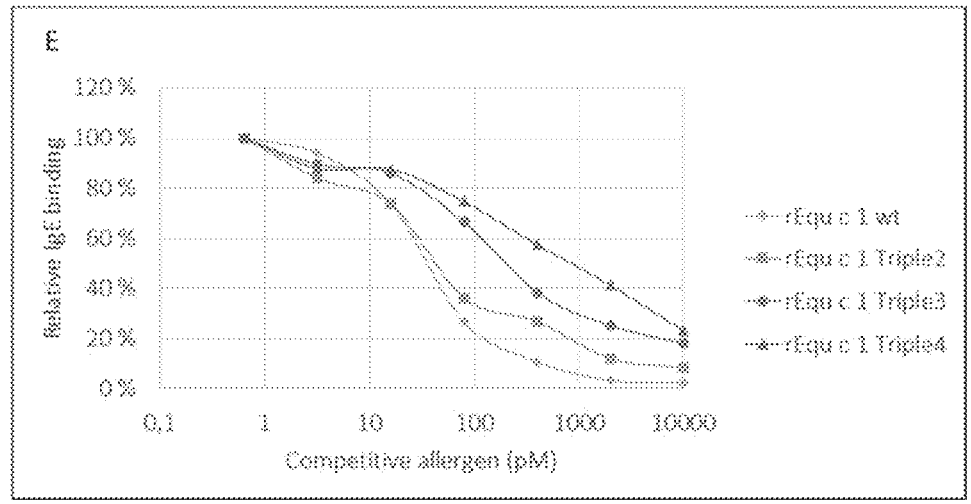

Example 5. IgE Binding to Recombinant Equ c 1 and Equ c 1 Mutant Polypeptides Analyzed by a Competitive Immunoassay The serum IgE binding to the wt rEqu c 1 and Triple 2, Triple 3 or Triple 4 mutants was analysed by a competitive miniaturized immunoassay. The binding of serum IgE to the biotinylated rEqu c 1 wt immobilized on streptavidin wells was inhibited by increasing amounts of soluble wt rEqu c 1 and Triple 2, 3 and 4 mutants. The wt rEqu c 1 was biotinylated using Sulfo-NHS-LC-biotin (Pierce) according to manufacturer's protocol. The biotinylated rEqu c 1 was spotted (375 pg) onto streptavidin (SA) wells (Pierce 15500). Serum samples (with pre-determined dilutions) from five patients allergic to horses were incubated with 0, 0.0006, 0.003, 0.016, 0.08, 0.4, 2.0 and 10 nM concentrations of wt rEqu c 1 or mutants Triple 2, Triple 3 and Triple 4 for 1h at RT in a shaker. Next, these serum samples were pipetted on the SA-wells in which the biotinylated rEqu c 1 was immobilized. After 1h incubation at RT and washing steps the bound IgE antibodies were detected with an anti-human IgE peroxidase conjugate stained with Alexa Fluor 647 Tyramide (ThermoFisher Scientific). The fluorescence read-out was carried out with Sensovation SensoSpot Microarray Analyzer. The rEqu c 1 mutants, Triple 2, 3 and 4, showed reduced inhibition when compared to the wt rEqu c 1 control, indicating that the mutations V47K and E21Y locate in the IgE epitope area of rEqu c 1 allergen and that the monomeric form of Triple 2, 3 and 4 mutants enhance also the lower binding inhibition (FIG. 3).

Example 6. Basophil Activation Test

Figure 4:
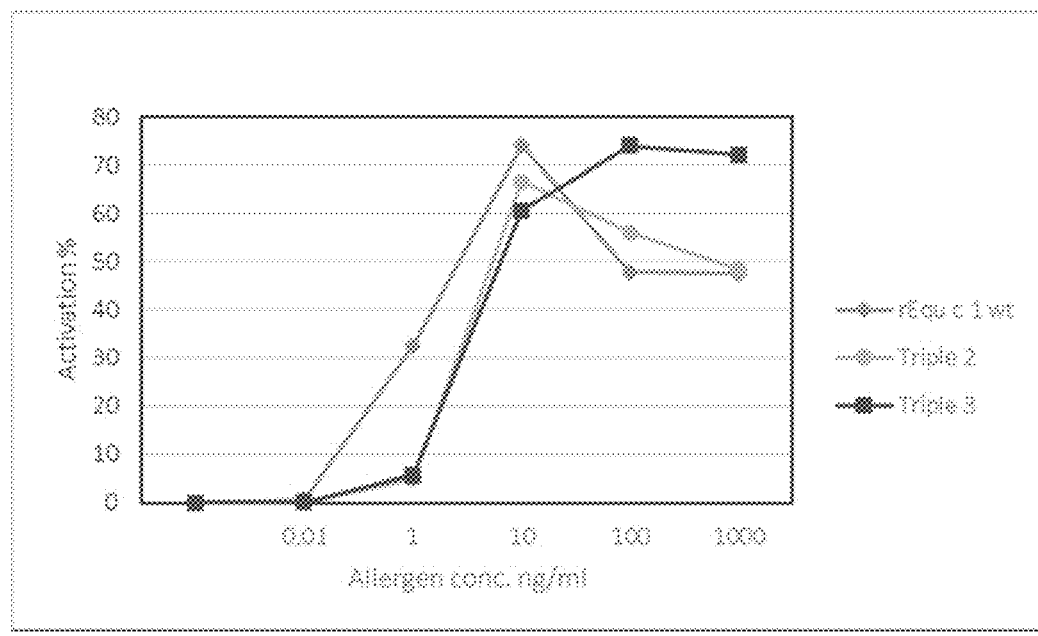
FIG. 4 shows the result of the basophil activation test with rEqu c 1 wt, Triple 2 and Triple 3 mutants.

Basophil activation test (BAT) was performed with the blood sample of Patient 1. Blood sample was incubated with (1000, 100, 10, 1 and 0.1 ng/ml) wt and Triple 2, 3 and 4 rEqu c 1 allergens. The percentage of activated basophils was determined by flow cytometry by analysing the expressed CD63 marker after the in vitro stimulation by the allergens. The rEqu c 1 mutants Triple 2 and 3 shows reduced basophil activation within the concentration range of 0.1-10 ng/ml when compared to the wt rEq c 1 (FIG. 4).

Example 7. Histamine Release Assay

Figures 5A, 5B, 5C:
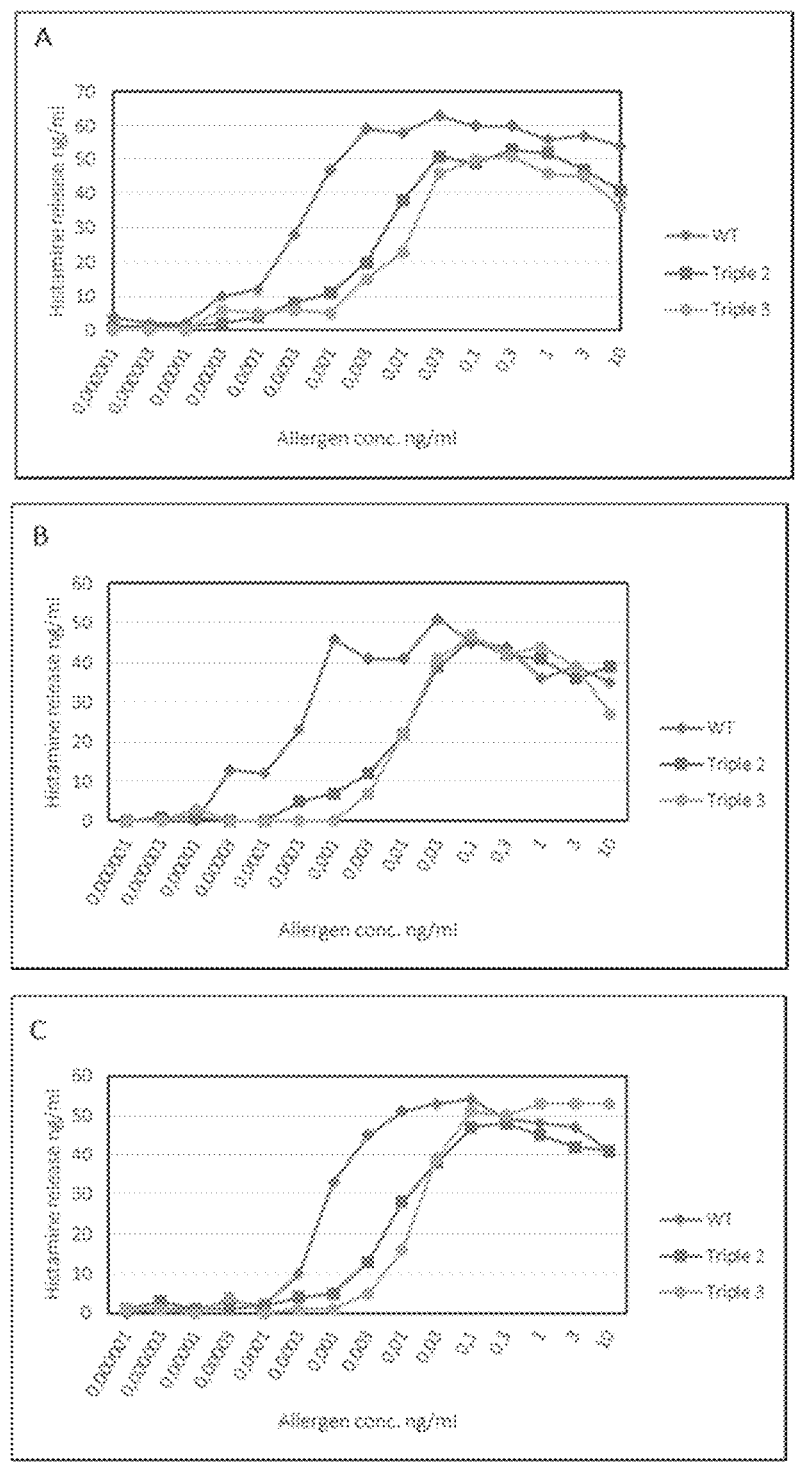
FIG. 5. Histamine release induced by rEqu c 1 wt, Triple 2 and Triple 3 mutants. Released histamine was measured after the passive sensitization of stripped basophils with sera of five horse allergic persons (A, B, C, D, E), RefLab's control serum (F) and serum of a non-allergic person (G).
Figures 5D, 5E, 5F, 5G:
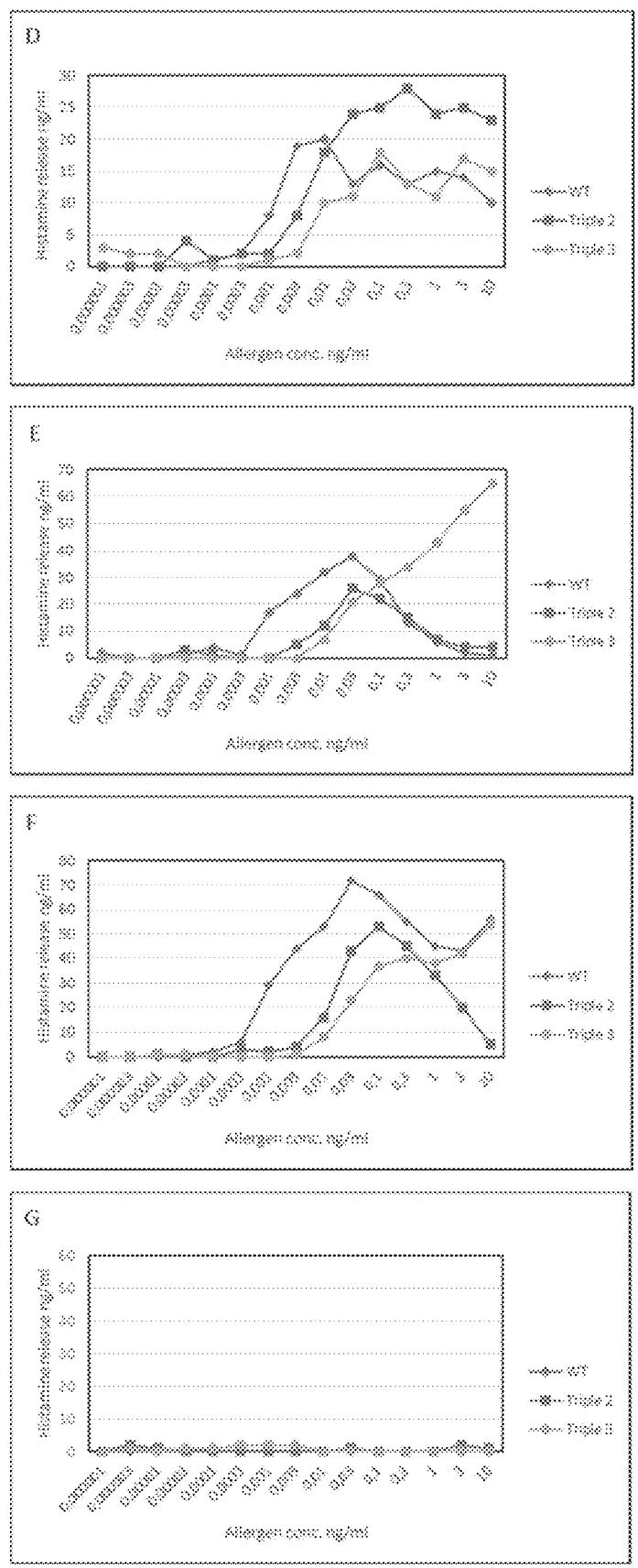

Biological activity of the rEqu c 1 wt, Triple 2 and Triple 3 mutants was analysed by a histamine release assay (HRA). HRA was performed as an outsourced service at RefLab Aps (Copenhagen, Denmark). Briefly, stripped human basophils were passively sensitized with the allergen polypeptides in 16 different concentrations (from 0.0000001 to 10 ng/ml) using five sera from horse allergic persons, one from a non-allergic person and a positive control serum from RefLab. Histamine released from the sensitized basophils was detected by a glass fiber method developed at RefLab. The results of the HRA indicate that the biological activity of rEqu c 1 Triple 2 and Triple 3 mutants is lower compared to the rEqu c 1 wt with all tested serum samples of horse allergic persons (FIG. 5).

Figure 6:
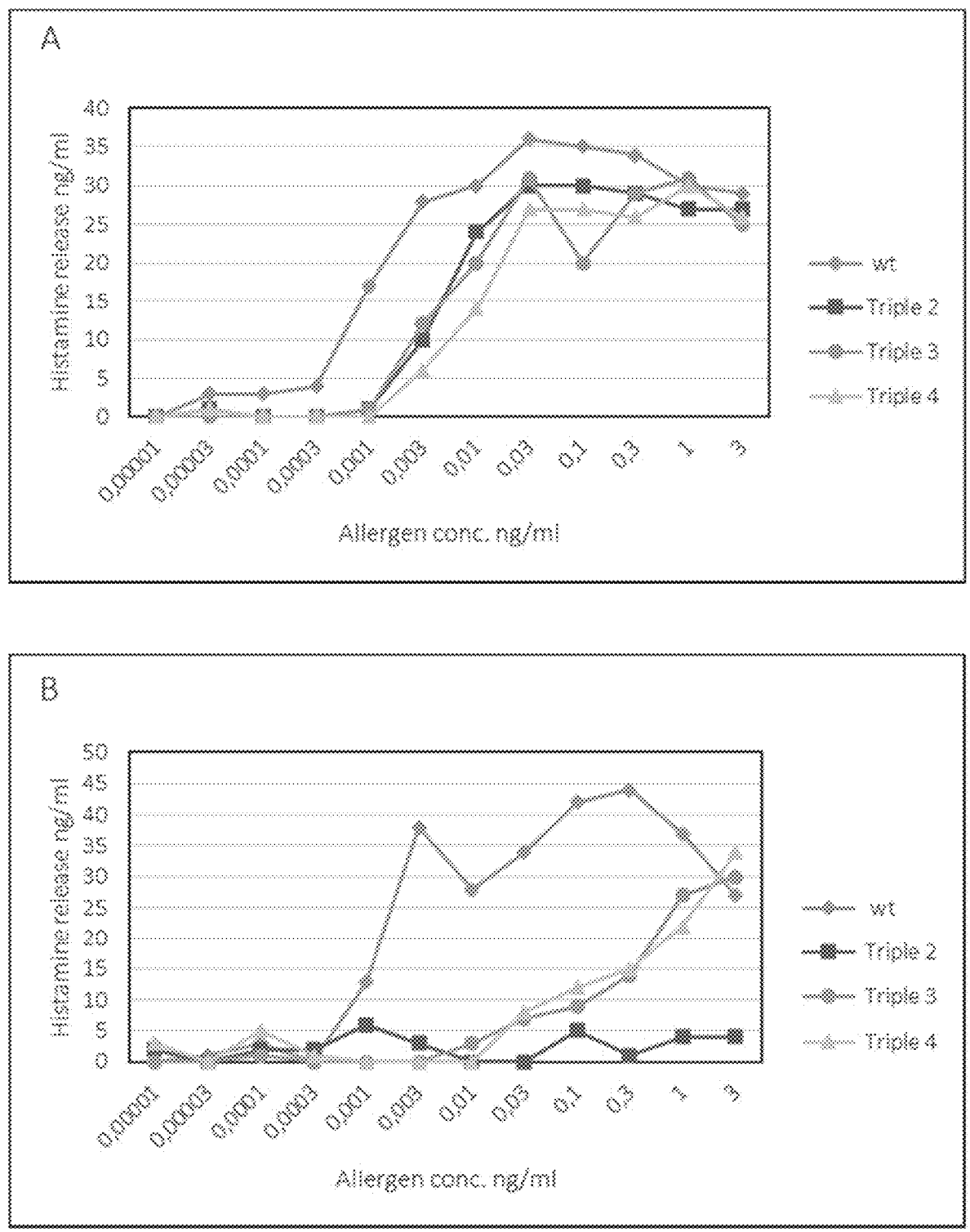
FIG. 6. Histamine release induced by rEqu c 1 wt, Triple 2, Triple 3 and Triple 4 mutants. Released histamine was measured after direct sensitization of basophils from two horse allergic persons (A, B).
Figure 7:
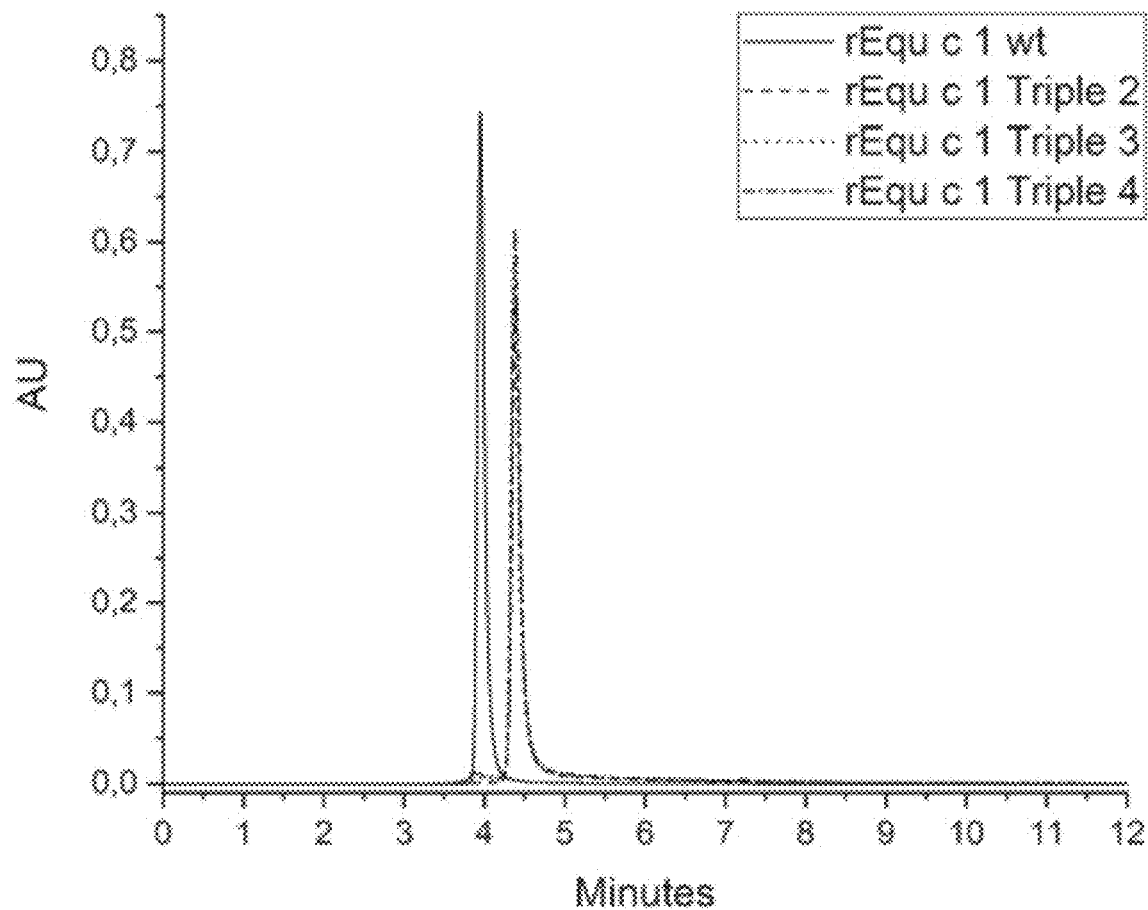
FIG. 7. The SEC-UHPLC elution profiles of Equ c 1 allergens: wt, Triple 2, 3 and Triple 4 measured at the concentration of 40 μM.

The biological activity of rEqu c 1 allergens, wt, Triple 2, Triple 3 and Triple 4 was further analysed by a direct HRA at RefLab Aps. Briefly, the basophil leukocytes of the blood samples from two horse allergic persons were challenged with rEqu c 1 allergens in 12 different concentrations (from 0.00001 to 3 ng/ml). Histamine released from the basophils was detected by a glass fiber method developed at RefLab. The results of the direct HRA further confirmed that the biological activity of rEqu c 1 Triple 2, Triple 3 and also Triple 4 mutants is lower compared to the rEqu c 1 wt (FIG. 6).

Example 8. Size-Exclusion Ultra-High-Performance Liquid Chromatography (SE-UHPLC) Analysis of rEqu c 1 wt and Mutants Size-exclusion ultra-high-performance liquid chromatography (SE-UHPLC) analysis of rEqu c 1 wt and mutants was performed using Acquity BEH125 SEC column with dimensions of 4.6×150 mm, a pore size of 125 Å and a particle size of 1.7 μm (Waters) coupled with Acquity I-Class UPLC instrument (Waters). The column was equilibrated to running conditions with PBS (12 mM $Na_2HPO_4$, 3 mM $NaH_2PO_4$, 150 mM NaCl pH 7.3) as a mobile phase at flow rate 0.3 ml/min until the baseline was stable. Sample amounts of 2 µl from a 40 µM protein solution were injected. The chromatographic separation was carried out under isocratic flow with overall run time of 12 minutes and detection at 214 nm wavelength. For gel filtration standard, the BEH125 SEC Protein Standard Mix (Waters) was used. SE-UHPLC results show that the hypoallergen mutants (Triple 2, 3, and 4) exist mainly as monomers whereas wild type exists mainly as a dimer at the concentration of 40 µM (FIG. 7).

REFERENCES

Arango et al., 1992, Eur J Biochem, 205(2):575-81
Goubran Botros et al., 2001, Eur. J. Biochem, 268:3126-3136
Hoffmann-Sommergruber et al., 1997, Protein Expr Purif, 9(1):33-9
layer et al., Cell 1990(61):553-556
Niederberger et al., PNAS, 101 (2): 14677-82, 2004
Niemi et al., Structure 2007(15): 1413-21
Remington's Pharmaceutical Sciences, 22nd edition, Allen, Loyd V., Jr, Ed., (2012)
Rouvinen et al., PloS ONE 2010(5):e9037
Stancombe et al., 2003, Protein Expr Purif, 30(2):283-92
Trevino et al., 2007, Journal of Molecular Biology 366:449-460
Tuschl, T. (2002), Nat. Biotechnol, 20: 446-448
EP 1812059
US 2009/0297564
WO 04/047794
WO 2008/092992
WO 2009/153414

The invention claimed is:

1. A recombinant hypoallergenic Equ c 1 polypeptide consisting of SEQ ID NO:1 with one or more amino acid modifications compared to a corresponding wild type Equ c 1 allergen, wherein the recombinant hypoallergenic polypeptide activates release of histamine from basophils to a degree less than the wild type Equ c 1 allergen, wherein said one or more amino acid modifications are one or more single amino acid substitutions selected from the group consisting of E21Y, V47K, V110E, V110D, F112K, and F112R.

2. The recombinant polypeptide according to claim 1, wherein said one or more single amino acid substitutions are selected from the group consisting of: V110E and V110D.

3. The recombinant polypeptide according to claim 1, wherein said one or more single amino acid substitutions are selected from the group consisting of: F112K and F112R.

4. The recombinant polypeptide according to claim 1, wherein said one or more amino acid substitutions consist of at least one amino acid substitution selected from the group consisting of: E21Y and V47K, at least one amino acid substitution selected from the group consisting of: V110E, V110D, and at least one amino acid substitution selected from the group consisting of: F112K and F112R.

5. The recombinant polypeptide according to claim 1, wherein said one or more amino acid substitutions are E21Y, V110E and F112K.

6. The recombinant polypeptide according to claim 1, wherein said one or more amino acid substitutions are V47K, V110E and F112K.

7. The recombinant polypeptide according to claim 1, wherein said one or more amino acid substitutions are E21Y, V110D and F112R.

8. The recombinant polypeptide according to claim 1, having a histamine release capacity which is at least 20 times reduced when compared to the histamine release capacity of the wild type Equ c 1 allergen.

9. The recombinant polypeptide according to claim 8, having a histamine release capacity which is at least 100 times reduced when compared to the histamine release capacity of the wild type Equ c 1 allergen.

10. A pharmaceutical composition comprising the recombinant hypoallergenic Equ c 1 polypeptide according to claim 1 and at least one of the following selected from the group consisting of: a physiologically acceptable adjuvant, carrier, diluent, excipient, preservative, and a stabilizer.

11. A method of treating horse allergy in a subject, the method comprising: administering to the subject an amount of the recombinant hypoallergenic Equ c 1 polypeptide according to claim 1 in an amount effective to ameliorate at least one symptom or clinical sign of allergy to an Equ c 1 allergen, wherein the recombinant hypoallergenic Equ c 1 polypeptide activates release of histamine from basophils to a degree less than the wild type Equ c 1 allergen.

* * * * *

SEQUENCE LISTING

```
<160> NUMBER OF SEQ ID NOS: 4

<210> SEQ ID NO 1
<211> LENGTH: 172
<212> TYPE: PRT
<213> ORGANISM: Equus caballus

<400> SEQUENCE: 1

Gln Gln Glu Glu Asn Ser Asp Val Ala Ile Arg Asn Phe Asp Ile Ser
1               5                   10                  15

Lys Ile Ser Gly Glu Trp Tyr Ser Ile Phe Leu Ala Ser Asp Val Lys
            20                  25                  30

Glu Lys Ile Glu Glu Asn Gly Ser Met Arg Val Phe Val Asp Val Ile
        35                  40                  45

Arg Ala Leu Asp Asn Ser Ser Leu Tyr Ala Glu Tyr Gln Thr Lys Val
    50                  55                  60

Asn Gly Glu Cys Thr Glu Phe Pro Met Val Phe Asp Lys Thr Glu Glu
65                  70                  75                  80

Asp Gly Val Tyr Ser Leu Asn Tyr Asp Gly Tyr Asn Val Phe Arg Ile
                85                  90                  95

Ser Glu Phe Glu Asn Asp Glu His Ile Ile Leu Tyr Leu Val Asn Phe
            100                 105                 110

Asp Lys Asp Arg Pro Phe Gln Leu Phe Glu Phe Tyr Ala Arg Glu Pro
        115                 120                 125

Asp Val Ser Pro Glu Ile Lys Glu Glu Phe Val Lys Ile Val Gln Lys
    130                 135                 140

Arg Gly Ile Val Lys Glu Asn Ile Ile Asp Leu Thr Lys Ile Asp Arg
145                 150                 155                 160

Cys Phe Gln Leu Arg Gly Asn Gly Val Ala Gln Ala
                165                 170

<210> SEQ ID NO 2
<211> LENGTH: 173
<212> TYPE: PRT
<213> ORGANISM: Artificial Sequence
<220> FEATURE:
<223> OTHER INFORMATION: Modified Equ c 1 allergen, Triple 2

<400> SEQUENCE: 2

Ala Gln Gln Glu Glu Asn Ser Asp Val Ala Ile Arg Asn Phe Asp Ile
1               5                   10                  15
```

-continued

```
Ser Lys Ile Ser Gly Glu Trp Tyr Ser Ile Phe Leu Ala Ser Asp Val
            20                  25                  30

Lys Glu Lys Ile Glu Glu Asn Gly Ser Met Arg Val Phe Val Asp Lys
        35                  40                  45

Ile Arg Ala Leu Asp Asn Ser Ser Leu Tyr Ala Glu Tyr Gln Thr Lys
    50                  55                  60

Val Asn Gly Glu Cys Thr Glu Phe Pro Met Val Phe Asp Lys Thr Glu
65                  70                  75                  80

Glu Asp Gly Val Tyr Ser Leu Asn Tyr Asp Gly Tyr Asn Val Phe Arg
                85                  90                  95

Ile Ser Glu Phe Glu Asn Asp Glu His Ile Ile Leu Tyr Leu Glu Asn
            100                 105                 110

Lys Asp Lys Asp Arg Pro Phe Gln Leu Phe Glu Phe Tyr Ala Arg Glu
        115                 120                 125

Pro Asp Val Ser Pro Glu Ile Lys Glu Glu Phe Val Lys Ile Val Gln
    130                 135                 140

Lys Arg Gly Ile Val Lys Glu Asn Ile Ile Asp Leu Thr Lys Ile Asp
145                 150                 155                 160

Arg Cys Phe Gln Leu Arg Gly Asn Gly Val Ala Gln Ala
                165                 170
```

<210> SEQ ID NO 3
<211> LENGTH: 173
<212> TYPE: PRT
<213> ORGANISM: Artificial Sequence
<220> FEATURE:
<223> OTHER INFORMATION: Modified Equ c 1 allergen, Triple 3

<400> SEQUENCE: 3

```
Ala Gln Gln Glu Glu Asn Ser Asp Val Ala Ile Arg Asn Phe Asp Ile
1               5                   10                  15

Ser Lys Ile Ser Gly Tyr Trp Tyr Ser Ile Phe Leu Ala Ser Asp Val
            20                  25                  30

Lys Glu Lys Ile Glu Glu Asn Gly Ser Met Arg Val Phe Val Asp Val
        35                  40                  45

Ile Arg Ala Leu Asp Asn Ser Ser Leu Tyr Ala Glu Tyr Gln Thr Lys
    50                  55                  60

Val Asn Gly Glu Cys Thr Glu Phe Pro Met Val Phe Asp Lys Thr Glu
65                  70                  75                  80

Glu Asp Gly Val Tyr Ser Leu Asn Tyr Asp Gly Tyr Asn Val Phe Arg
                85                  90                  95

Ile Ser Glu Phe Glu Asn Asp Glu His Ile Ile Leu Tyr Leu Glu Asn
            100                 105                 110

Lys Asp Lys Asp Arg Pro Phe Gln Leu Phe Glu Phe Tyr Ala Arg Glu
        115                 120                 125

Pro Asp Val Ser Pro Glu Ile Lys Glu Glu Phe Val Lys Ile Val Gln
    130                 135                 140

Lys Arg Gly Ile Val Lys Glu Asn Ile Ile Asp Leu Thr Lys Ile Asp
145                 150                 155                 160

Arg Cys Phe Gln Leu Arg Gly Asn Gly Val Ala Gln Ala
                165                 170
```

<210> SEQ ID NO 4
<211> LENGTH: 173
<212> TYPE: PRT
<213> ORGANISM: Artificial Sequence
<220> FEATURE:

```
<223> OTHER INFORMATION: Modified Equ c 1 allergen, Triple 4

<400> SEQUENCE: 4

Ala Gln Gln Glu Glu Asn Ser Asp Val Ala Ile Arg Asn Phe Asp Ile
1               5                   10                  15

Ser Lys Ile Ser Gly Tyr Trp Tyr Ser Ile Phe Leu Ala Ser Asp Val
            20                  25                  30

Lys Glu Lys Ile Glu Glu Asn Gly Ser Met Arg Val Phe Val Asp Val
        35                  40                  45

Ile Arg Ala Leu Asp Asn Ser Ser Leu Tyr Ala Glu Tyr Gln Thr Lys
    50                  55                  60

Val Asn Gly Glu Cys Thr Glu Phe Pro Met Val Phe Asp Lys Thr Glu
65                  70                  75                  80

Glu Asp Gly Val Tyr Ser Leu Asn Tyr Asp Gly Tyr Asn Val Phe Arg
                85                  90                  95

Ile Ser Glu Phe Glu Asn Asp Glu His Ile Ile Leu Tyr Leu Asp Asn
                100                 105                 110

Arg Asp Lys Asp Arg Pro Phe Gln Leu Phe Glu Phe Tyr Ala Arg Glu
        115                 120                 125

Pro Asp Val Ser Pro Glu Ile Lys Glu Glu Phe Val Lys Ile Val Gln
    130                 135                 140

Lys Arg Gly Ile Val Lys Glu Asn Ile Ile Asp Leu Thr Lys Ile Asp
145                 150                 155                 160

Arg Cys Phe Gln Leu Arg Gly Asn Gly Val Ala Gln Ala
                165                 170
```